United States Patent
Fukami et al.

(10) Patent No.: US 10,101,309 B2
(45) Date of Patent: Oct. 16, 2018

(54) EXHAUST GAS ANALYZING APPARATUS

(71) Applicant: HORIBA, Ltd., Kyoto (JP)

(72) Inventors: Shun Fukami, Kyoto (JP); Shintaro Aoki, Kyoto (JP); Toshio Ohta, Kyoto (JP)

(73) Assignee: Horiba Ltd., Kyoto (JP)

( * ) Notice: Subject to any disclaimer, the term of this patent is extended or adjusted under 35 U.S.C. 154(b) by 69 days.

(21) Appl. No.: 14/713,901

(22) Filed: May 15, 2015

(65) Prior Publication Data
US 2015/0330868 A1 Nov. 19, 2015

(30) Foreign Application Priority Data

May 15, 2014 (JP) .................................. 2014-101176

(51) Int. Cl.
*G01N 33/00* (2006.01)
*G01N 1/22* (2006.01)
(Continued)

(52) U.S. Cl.
CPC ....... *G01N 33/0016* (2013.01); *G01N 1/2252* (2013.01); *G01N 21/33* (2013.01);
(Continued)

(58) Field of Classification Search
CPC .. G01N 1/2252; G01N 21/33; G01N 21/3504; G01N 21/76; G01N 33/0016;
(Continued)

(56) References Cited

U.S. PATENT DOCUMENTS 5,543,113 A * 8/1996 Koike ................ G01N 33/0006
422/83
6,439,040 B1 8/2002 Garms et al.
(Continued)

FOREIGN PATENT DOCUMENTS

JP 2002-340778 A 11/2002

OTHER PUBLICATIONS

Non-Patent Literature "Environmental Protection Agency", 40 CFR 92.114, Jul. 2012 edition.*
(Continued)

*Primary Examiner* — Lisa Caputo
*Assistant Examiner* — Irving A Campbell
(74) *Attorney, Agent, or Firm* — Brooks Kushman P.C.

(57) ABSTRACT

An exhaust gas analyzing apparatus of a vehicle mounted type equipped with an analyzer that is configured to analyze components contained in exhaust gas includes a sampling line that is an exhaust gas flow path extending from an exhaust gas introduction terminal that is configured to introduce the exhaust gas from the outside to the analyzer; a pressure reduction source that is configured to reduce a pressure in the sampling line to a predetermined pressure; and a temperature-regulating mechanism that is configured to regulate a temperature of the exhaust gas flowing in the sampling line to be at least a first temperature. The first temperature is set to be a temperature equal to or higher than an evaporation temperature of moisture at the reduced predetermined pressure and lower than an evaporation temperature of moisture at one atmospheric pressure.

11 Claims, 5 Drawing Sheets

(51) Int. Cl.
    *G01N 21/33*         (2006.01)
    *G01N 21/3504*     (2014.01)
    *G01N 21/76*         (2006.01)

(52) U.S. Cl.
    CPC .......... *G01N 21/3504* (2013.01); *G01N 21/76* (2013.01); *G01N 2001/2261* (2013.01); *G01N 2021/354* (2013.01); *G01N 2201/0216* (2013.01)

(58) Field of Classification Search
    CPC ..... G01N 2001/2201; G01N 2021/354; G01N 2201/0216; G01N 2001/2261; G01M 15/102; G01M 15/108; G01M 15/10
    USPC ......... 73/23.2, 23.31, 23.32, 114.69–114.76, 73/24.04, 31.05, 114.69–114.73, 23.3; 60/274, 276, 315
    See application file for complete search history.

(56) References Cited

U.S. PATENT DOCUMENTS

| | | | |
|---|---|---|---|
| 2004/0064243 A1* | 4/2004 | Nakamura | F01N 13/008 701/114 |
| 2005/0274169 A1 | 12/2005 | Butler et al. | |
| 2006/0236752 A1* | 10/2006 | Nakamura | G01N 33/0032 73/23.21 |
| 2008/0298788 A1* | 12/2008 | Martucci | F16L 53/008 392/472 |
| 2011/0285998 A1 | 11/2011 | Hara et al. | |
| 2013/0312486 A1* | 11/2013 | Nakagawa | G01N 1/2252 73/23.31 |

OTHER PUBLICATIONS

EESR dated Oct. 16, 2015 issued for European patent application No. 15 167 506.3, 6 pgs.

* cited by examiner

EXHAUST GAS ANALYZING APPARATUS

CROSS-REFERENCE TO RELATED APPLICATION

This application claims priority to JP Application No. 2014-101176, filed May 15, 2014, the disclosure of which is incorporated in its entirety by reference herein.

TECHNICAL FIELD

The present invention relates to a vehicle mounted type exhaust gas analyzing apparatus equipped with an analyzer that is configured to components contained in the exhaust gas.

BACKGROUND ART

For example, in the case where a concentration of moisture contained in the exhaust gas is measured by a non-dispersive infrared absorption (NDIR) method, the exhaust gas is cooled and the moisture is condensed, and this results in an erroneous measurement value different from that of the original one. In order to prevent such an erroneous measurement, a sampling line up to reach the moisture concentration meter is heated in some cases (JP2002-340778A).

In this configuration, it is configured that the temperature of the exhaust gas in the sampling line is regulated to be equal to or higher than 100° C. to thereby prevent the moisture contained in the exhaust gas from being condensed. Further, even in the case where only the concentration other than the moisture contained in the exhaust gas is measured, when the concentration of the moisture is largely changed, the measurement accuracy of the other components is affected. Therefore, it is configured so that the temperature of the exhaust gas in the sampling line is also regulated to be equal to or higher than 100° C.

However, since the vehicle mounted type exhaust gas analyzing apparatus uses, for example, a battery of the vehicle as a power supply source thereof and the power capacity is limited. Therefore, in the case where a large power consumption occurs in such a temperature regulation mechanism, an operational time of the exhaust gas analyzing apparatus is extremely limited and it is difficult to perform a sufficient exhaust gas analysis.

SUMMARY OF INVENTION

Technical Problem

Therefore, the present invention has been made in consideration of the above problems, and an essential object thereof is to provide an exhaust gas analyzing apparatus capable of preventing condensation of moisture until exhaust gas reaches an analyzer and allowing to perform an accurate analysis with remarkable reduction of a power consumption in a temperature regulation of the exhaust gas.

Solution to Problem

That is, in one aspect of the present invention, an exhaust gas analyzing apparatus of a vehicle mounted type is equipped with an analyzer for analyzing components contained in exhaust gas. The exhaust gas analyzing apparatus includes:

a sampling line that is an exhaust gas flow path extending from an exhaust gas introduction terminal that is configured to introduce the exhaust gas from the outside to the analyzer;

a pressure reduction source that is configured to reduce a pressure in the sampling line to a predetermined pressure; and a temperature-regulating mechanism that is configured to regulate a temperature of the exhaust gas flowing in the sampling line to be at least a first temperature, wherein the first temperature is set to be a temperature equal to or higher than an evaporation temperature of moisture at the reduced predetermined pressure and lower than an evaporation temperature of moisture at one atmospheric pressure.

With this configuration, since the exhaust gas flowing in the sampling line is reduced in pressure to be in a state of easily evaporable than in a normal state, condensation of the moisture can be prevented from occurrence in the sampling line and the analyzer even though the first temperature is set to be lower than, for example, 100° C.

Further, since the first temperature is set to be lower compared to conventional one, the power consumption amount due to the temperature regulation is also remarkably reduced and it is possible to ensure a sufficient operable time even in a vehicle mounted type exhaust gas analyzing apparatus having a limited power capacity such as a battery.

In order to prevent condensation of moisture contained in the exhaust gas from occurring until the exhaust gas reaches the analyzer even in the case where the concentration of the moisture of the exhaust gas is extremely high or in the case where an external environment of the vehicle is peculiar, it is sufficient that the temperature-regulating mechanism is configured to regulate the temperature of the exhaust gas at a second temperature that is higher than the first temperature under a predetermined condition.

At a time of performing a cold start operation in which an engine is started in a state that an exhaust pipe and the like is cold after the engine of a vehicle is stopping for a long time, the condensation of the moisture easily occurs and a large amount of water droplets may be contained in the exhaust gas in some cases. The water droplets generated at the time of cold start may be vaporized during the subsequent analysis of the continuous exhaust gas, which may appear as a large error in the analysis data in some cases. In order to solve this problem by preventing the water droplets generated at the time of cold start from remaining in the sampling line and the analyzer, it is sufficient that the temperature-regulating mechanism is configured to regulate the temperature of the exhaust gas at the second temperature in the case where a vehicle performs a cold start operation.

Making use of a fact that easiness of condensation of the moisture contained in the exhaust gas is also affected by an amount of the atmospheric pressure, in order to further reduce the power consumption amount in the temperature-regulating mechanism while preventing the condensation of the moisture contained in the exhaust gas, it is sufficient that the temperature-regulating mechanism is equipped with a heating wire heater that is configured to regulate a temperature of the sampling line and a temperature setting part that is configured to set a set temperature which is a target value to be set to the heating wire heater, and wherein the temperature setting part is configured to change the set temperature in accordance with an atmospheric pressure.

The concentration of moisture contained in the exhaust gas is largely different dependent on which type of the engine is used, for example, a gasoline engine or a diesel engine. In consideration of easiness of condensation of the moisture due to difference of types of the internal combustion engines mounted on the vehicles in this way, in order to be able to reduce the power consumption in the temperature-regulating mechanism while preventing the condensation of the moisture, it is sufficient that the temperature setting part is configured to change the set temperature in accordance with a type of an internal combustion engine of the vehicle.

The concentration of the moisture contained in the exhaust gas may be suddenly increased for any reason to affect significantly on the analysis of the analyzer in some cases. In order to possibly prevent such influence from appearing on the analysis while preventing the condensation of the moisture even in the case where such a sudden change of the concentration of the moisture occurs, it is sufficient that, the analyzer is adapted to analyze a concentration of the moisture contained in the exhaust gas, and wherein the temperature setting part is configured to change the set temperature in accordance with an indication value of the analyzer.

Effects of Invention

According to the exhaust gas analyzing apparatus of the present invention, since the pressure in the sampling line is reduced by the pressure reduction source and the temperature regulation is performed by the temperature regulating mechanism in a state that the first temperature is set to be lower than that in the conventional case. Therefore, the condensation of the moisture contained in the exhaust gas can be prevented and the power consumption consumed by the temperature regulating mechanism can be remarkably reduced.

DESCRIPTION OF EMBODIMENTS

The following describes an exhaust gas analyzing apparatus 5 and an exhaust gas analyzing system 200 according to one embodiment of the present invention with reference to the accompanying drawings.

Figure 1:
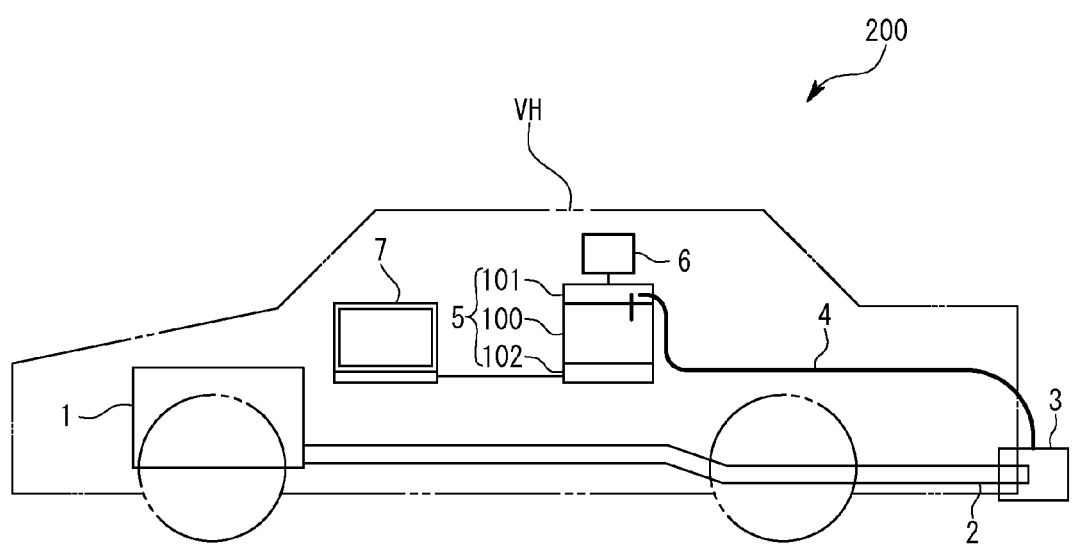
FIG. 1 is a schematic diagram showing an exhaust gas analyzing apparatus and exhaust gas analyzing system according to one embodiment of the present invention.

The exhaust gas analyzing system 200 according to the present embodiment is vehicle mounted type one that is adapted to analyze components such as carbon monoxide (CO), carbon dioxide ($CO_2$), water ($H_2O$), nitrogen oxides (NOX) and total hydrocarbon (THC) contained in the exhaust gas discharged from an exhaust pipe 2 which is connected to an internal combustion engine 1 of a vehicle VH as shown in FIG. 1. It is noted here that the term "analyze" implies a concept including detection of presence or absence of each analysis target substance and measurement of concentration thereof and the like.

Specifically, as shown in FIG. 1, the exhaust gas analyzing system 200 is configured of an exhaust gas sampling mechanism 3 which is attached to an opening side end of the exhaust pipe 2, the exhaust gas analyzing apparatus 5 mounted in a vehicle, a hot hose 4 for introducing the exhaust gas sampled by the exhaust gas sampling mechanism 3 to the exhaust gas analyzing apparatus 5 while keeping the exhaust gas at a predetermined temperature and a power supply switching device 6 which is connected to the battery of the vehicle VH of another battery for supplying electric power to the exhaust gas analyzing apparatus 5. The hot hose 4 includes: an inner tube made of plastic or metallic; a heating wire which is provided along an outer peripheral surface of the inner tube; and a heat insulating member which is provided so as to cover the outside of the inner tube and the heating wire. This hot hose 4 has one end connected to the exhaust gas sampling mechanism 3 attached to the outside of the vehicle VH and guided into a trunk room passing through a hole such as a weep hole provided in the trunk room of the vehicle VH. Further, the other end of the hot hose 4 is guided from the trunk room to a sheeted inside of the vehicle and connected to the exhaust gas analyzing apparatus 5.

Figure 2:
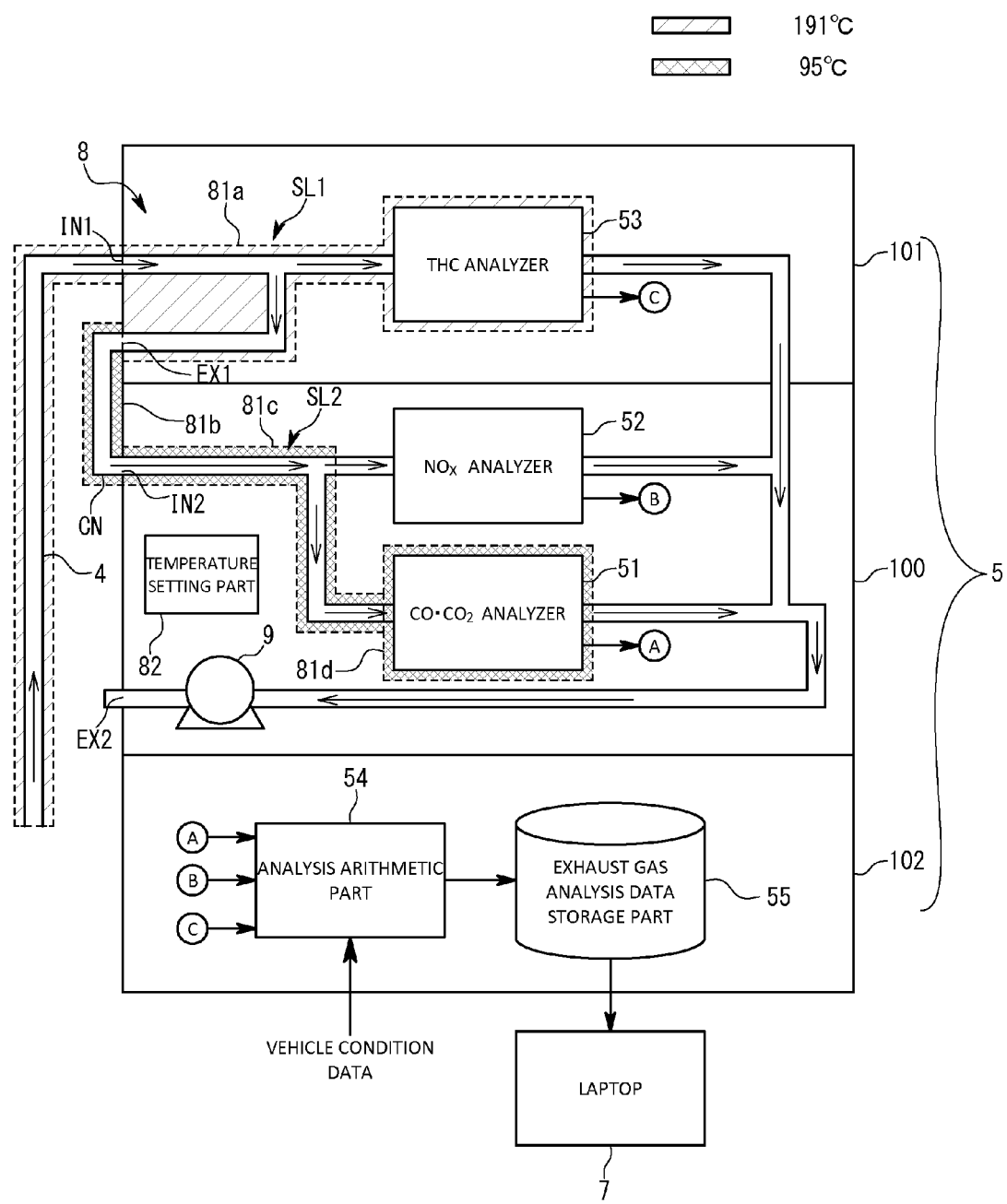
FIG. 2 is a schematic diagram showing details of the exhaust gas analyzing apparatus in the same embodiment.

The following describes the exhaust gas analyzing apparatus 5 with reference to FIG. 2.

The exhaust gas analyzing apparatus 5 is configured of: an exhaust gas analyzing apparatus main body 100 (also, referred to as "main body 100" hereinafter); an extension analysis unit 101; and an arithmetic storage unit 102. The main body 100 is adapted to analyze the carbon monoxide, carbon dioxide, moisture and nitrogen oxide contained in the exhaust gas. The extension analysis unit 101 is detachably fixed to the main body 100 and analyzes hydro carbon contained in the exhaust gas. The arithmetic storage unit 102 receives output signals from the main body 100 and the extension analysis unit 101 and performs the process and storage of respectively analyzed data.

As shown in FIG. 2, the exhaust gas analyzing apparatus 5 is configured by laminating the arithmetic storage unit 102, main body 100 and extension analysis unit 101 in this order from the bottom side, and the arithmetic storage unit 102 and extension analysis unit 101 are integrally fixed with respect to the main body 100. Thus, as shown in FIG. 2, the exhaust gas sampled by the exhaust gas sampling mechanism 3 is first guided to the extension analysis unit 101 through the hot hose 4. A part of the exhaust gas guided to the extension analysis unit 101 is split and introduced into the main body 100 through a connection pipe CN which is provided for connection between the extension analysis unit 101 and the main body 100. Then the exhaust gases used for analyses in the main body 100 and the extension analysis unit 101 meet together to be exhausted to the outside from an input/output surface of the exhaust gas analyzing apparatus 5.

The following describes each of the parts with reference to FIG. 2.

As shown in FIG. 2, the main body 100 accommodates a $CO.CO_2$ analyzer 51 and an NOX analyzer 52 inside the housing thereof.

The $CO.CO_2$ analyzer 51 is adapted to continuously measure a concentration of carbon monoxide or carbon dioxide contained in the exhaust gas by a non-dispersive infrared absorption (NDIR) method. This $CO.CO_2$ analyzer 51 is also configured so as to continuously measure a concentration of moisture contained in the exhaust gas as well and it is configured so as to exert a function also as a moisture concentration meter.

The NOX analyzer 52 is adapted to continuously measure a concentration of NOX contained in the exhaust gas by a chemiluminescent method. Note that the NOX analyzer 52 may be also configured so as to measure a concentration of NOX contained in the exhaust gas by a non-dispersive ultraviolet ray analysis (NDUV) method.

Next, the following describes the extension analysis unit 101.

As shown in FIG. 2, this extension analysis unit 101 is generally flat rectangular parallelepiped shaped, which includes a THC analyzer 53 inside thereof for continuously measuring a concentration of hydrocarbon contained in the exhaust gas by a hydrogen flame ionization detection (FID) method. The extension analysis unit 101 is attached to the main body 100 in the case where it is necessary to analyze the hydrocarbon. In the case where it is not necessary to analyze the hydrocarbon, the extension analysis unit 101 is in a state of being removed and the hot hose 4 is directly connected to an exhaust gas introduction terminal IN2 of the main body 100, and thus only the analyses of the carbon monoxide, carbon dioxide, nitrogen oxide and moisture are adapted to be performed.

Next, the following describes the arithmetic storage unit 102.

The arithmetic storage unit 102 receives the analyzed data signals outputted from the main body 100 and the extension analysis unit 101, performs the data processing of the analyzed data indicated by the analyzed data signals, stores the processed data after performing a predetermined arithmetic process and displays the processed data on the portable personal computer 7 in a predetermined aspect. That is, the portable personal computer exerts only a function as a display for displaying the results of the exhaust gas analysis and a function as an input device for changing a set with respect to the exhaust gas analyzing apparatus 5 but does not perform a substantial data process and the like.

More specifically, this arithmetic storage unit 102 is generally flat rectangular parallelepiped shaped, which has a function as a so-called computer including a CPU, a memory, input/output equipment and the like inside thereof. Then, upon execution of a program for analyzing the exhaust gas stored in the memory, the arithmetic storage unit 102 receives the analyzed data signals outputted from the respective analyzers 51, 52 and 53 and a running data signal obtained from the vehicle VH. Then, the arithmetic storage unit 102 is configured to exert a function as an analysis arithmetic part 54 for converting these received signals to the exhaust gas analysis data which is processed data in a predetermined format and a function as an exhaust gas analysis data storage part 55 for storing the analysis data calculated by the analysis arithmetic part 54.

The analysis arithmetic part 54 converts the signals outputted from the respective analyzers 51, 52 and 53 to specific measurement values and corrects an influences to the measurement values due to such as moisture based on the respective measurement values. Further, the analysis arithmetic part 54 is configured to combine the running data obtained from the vehicle VH and the respective measurement values to thereby output the combined resultant data as the final exhaust gas analyzed data.

The exhaust gas analysis data storage part 55 is adapted to store the final exhaust gas analyzed data outputted from the analysis arithmetic part 54 in a non-volatile memory. Note that the portable personal computer 7 is used only for accessing the exhaust gas analysis data storage part 55 and obtaining the final exhaust gas analyzed data to be displayed in a predetermined display format, but the portable personal computer 7 does not perform such as an arithmetic process as to the analyzed data indicated by the analysis data signals outputted from the main body 100 and the extension analysis unit 101.

Thus, since the arithmetic storage unit 102 is configured so as to be able to generate and store the exhaust gas analyzed data on a stand-alone without a portable personal computer, the analysis of the exhaust gas is never interrupted even in the case where the connection to the personal computer should be interrupted.

Next, the following describes a flow path configuration of the exhaust gas and a temperature regulation mechanism 8 in the exhaust gas analyzing apparatus 5 with reference to FIG. 2.

In the exhaust gas analyzing apparatus 5 of the present embodiment, there are provided: a first sampling line SL1; a connection pipe CN; a second sampling line SL2; and the temperature regulation mechanism 8. The first sampling line SL1 is an exhaust gas flow path from an exhaust gas introduction terminal IN1 of the extension analysis unit 101 connected with the hot hose 4 to the THC analyzer 53. The connection pipe CN connects between an exhaust gas split flow terminal EX1 of the extension analysis unit 101 and the exhaust gas introduction terminal IN2 of the main body 100. The second sampling line SL2 is an exhaust gas flow path from the exhaust gas introduction terminal IN2 of the main body 100 to the CO.CO2 analyzer 51. The temperature regulation mechanism 8 is adapted to regulate: the first sampling line SL1; the connection pipe CN; the second sampling line SL2; and the CO.CO2 analyzer 51 per se.

More specifically, the temperature regulation mechanism 8 is equipped with: the first sampling line SL1; the connection pipe CN; the second sampling line SL2; heating wire heaters 81a to 81d (represented by "81" hereinafter in the case where there is no need to be distinguished) attached to the CO.CO2 analyzer 51; and a temperature setting part 82 for setting a set temperature of the heating wire heater 81 to be a target value. Note that the temperature regulation mechanism 8 is configured so that the function of the control operation thereof is implemented by executing a temperature regulation program stored in the memory by a computer composed of a CPU, a memory, input/output means and the like.

Note that, the temperature setting part 82 in the temperature regulation mechanism 8 is not an indispensable configuration, but, for example, the heating wire heater 81 may be configured so as to operate only at the first temperature to be described later, or the heating wire heater 81 may be configured so as to operate switchable at the first and second temperatures to be described later. With the temperature setting part 82 as in the present embodiment, the heating wire heater 81 can be operated at various temperatures depending on a situation and it becomes possible to temperature-regulate of the exhaust gas more finely.

The heating wire heater 81 is configured so that the current or voltage applied for maintaining the set setting temperature is feedback-controlled.

The temperature setting part 82 is adapted to receive a setting signal inputted by a user using the personal computer 7 or setting means (not shown) and set the setting temperature which is a target value to be set to the heating wire heater 81. In the present embodiment, the temperature setting part 82 is configured so as to set any one of the first and second temperatures as the setting temperature of the heating wire heater 81, based on the received signal. Here, the first temperature is used at the time of normal analysis of the exhaust gas and the second temperature is used at the time of a cold start operation.

The set temperature to be set by the temperature setting part 82 is adapted to be differentiated depending on a place where the heating wire heater 81 is provided. That is, in the present embodiment, in a normal use state, the temperature of the exhaust gas is adapted to be kept at 191° C. in the hot hose 4 and the first sampling line SL1 up to the THC analyzer 53, and to be kept at 95° C. in the connection pipe CN branched from the first sampling line SL1 to the CO.CO2 analyzer 51, the second sampling line SL2 and the CO.CO2 analyzer 51 per se.

In other words, when in normal use, the temperature setting part 82 is adapted to set 191° C. as the first temperature to the heating wire heater 81a provided on the first sampling line SL1 and set 95° C. to the heating wire heaters 81b, 81c and 81d provided on the connection pipe CN, the second sampling line SL2 and the CO.CO2 analyzer 51, respectively.

Note that the set temperature to be set, by the temperature setting part 82, to the heating wire heater 81c provided on the second sampling line SL2 may be made different from the set temperature to be set to the heating wire heater 81d provided on the CO.CO2 analyzer 51. In this case, it is sufficient that, the upper the heating wire heater 81 positioned in the upstream side with respect to the exhaust gas flow, the higher the set temperature to be set to the heating wire heater 81. For example, it may be also possible to set 95° C. as the first temperature to the heating wire heaters 81b and 81c respectively for temperature-regulating the connection pipe CN and the second sampling line SL2 and to set 80° C. as the first temperature to the heating wire heater 81d for temperature-regulating the CO.CO2 analyzer 51. Upon setting the first temperature in this way, it is possible to achieve further lower power consumption as compared to the case of setting 95° C. as the first temperature to each of the heating wire heaters 81b, 81c and 81d.

Here, the following describes the first temperature to be set as the set temperature to the heating wire heater 81c when in the normal analyzing operation. In this configuration, the heating wire heater 81c is provided on the second sampling line SL2 which is the exhaust gas flow path extending from the connection pipe CN to the CO.CO2 analyzer 51 which also serves as a moisture concentration meter. In the present embodiment, in order that the exhaust gas is allowed to flow through the flow path in the exhaust gas analyzing apparatus 5, the pressure of the exhaust gas is reduced by the pressure reduction source 9 and the pressure of the exhaust gas in the second sampling line SL2 is reduced to be lower than the atmospheric pressure. That is, the saturated vapor pressure of the moisture in the second sampling line SL2 is reduced to be lower compared to that under one atmosphere and therefore the moisture is in a state of easily being boiled. Therefore, in the present embodiment, the first temperature is set to 95° C. as the target temperature of the exhaust gas in the second sampling line SL2, which is lower than 100° C. and higher than the boiling point of water under a predetermined pressure. Thus, it is adapted to reduce the power consumption consumed by the heating wire heater 81 while preventing the condensation of the moisture.

The reason why the first temperature is set to be 191° C. as the set temperature to be set to the heating wire heater 81a provided on the hot hose 4 and the first sampling line SL1 at the time of the normal analyzing operation is because the exhaust gas in the state suitable for the analysis of the THC analyzer 53 is to be supplied. Therefore, in the case where there is no need to perform an analysis by the THC analyzer 53, the temperature setting part 82 may be also adapted to set the first temperature to be set to the heating wire heater 81a provided on the first sampling line SL1 to a temperature lower than the temperature 191° C. or a temperature substantially the same as the first temperature to be set to the heating wire heater 81c provided on the second sampling line SL2. Note that the set temperature shown in the present embodiment is merely an example and the first temperature should not be limited to only 191° C. or 95° C. and the second temperature should not be limited to only 100° C. but various temperatures may be set as the first and second temperatures.

Thus, according to the exhaust gas analyzing apparatus 5 of the present embodiment, in the second sampling line SL2 up to reaching the CO.CO2 analyzer 51, since the exhaust gas pressure is reduced by the pressure reduction source 9 while the boiling point of water is lowered and the temperature of the exhaust gas is kept to be 95° C. lower than 100° C. which is a boiling point under one atmosphere during the normal analyzing operation, the condensation of moisture can be prevented and the power consumption can be reduced by the temperature regulation as compared to the conventional case.

Therefore, even though the power supply source is such as a battery having a limited power capacity as in the vehicle mounted type exhaust gas analyzing apparatus 5, the operational time thereof can be more extended than that of conventional one while ensuring an accurate analysis.

Next, the following describes the second temperature which is the set temperature to be set by the temperature setting part 82 at the time of the cold start operation for starting an engine from a state of a warm-up operation being not performed in the vehicle VH and the exhaust gas analyzing system 200.

At the time of the cold start operation, the exhaust gas with a large amount of moisture being condensed is supplied into the exhaust gas analyzing apparatus 5. Therefore, in order that the condensed moisture is vaporized and discharged to the outside, the temperature setting part 82 is required to set the second temperature to at least the heating wire heater 81c provided on the second sampling line SL2, the second temperature being higher than 95° C. which is the first temperature. For example, in the case where a temperature lower than 100° C. is set as the first temperature, the temperature setting part 82 is configured to set 100° C. as the second temperature.

Thus, according to the exhaust gas analyzing apparatus 5 of the present embodiment, since the temperature setting part 82 sets the second temperature which is higher than the first temperature to the heating wire heater at the time of the cold start operation, it is possible to quickly evaporate water droplets generated at the time of the cold start operation to thereby prevent an influence thereof from appearing on the analysis to be performed later.

Other embodiments are described below.

Figure 3:
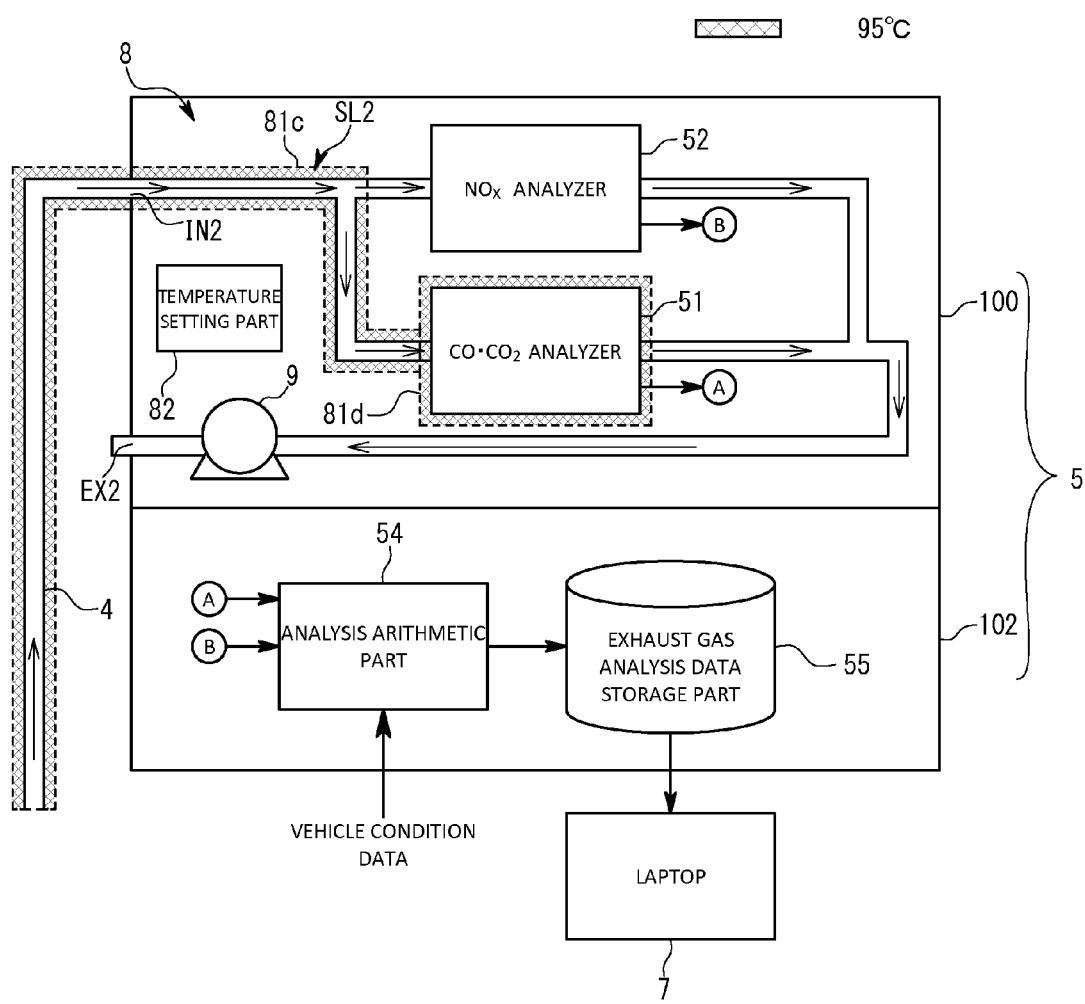
FIG. 3 is a schematic diagram showing details of an exhaust gas analyzing apparatus according to another embodiment of the present invention.

As shown in FIG. 3, the extension analysis unit 101 shown in FIG. 2 is removed and the hot hose 4 is directly connected to the exhaust gas introduction terminal IN2 of the main body 100, and the analyses of carbon monoxide, carbon dioxide, moisture and nitrogen oxides contained in the exhaust gas are performed only by the main body 100. In this configuration, the temperature of the exhaust gas may be set to a temperature lower than 191° C. in the flow path from a portion of the hot hose 4.

Also, it is not necessary to temperature-regulate the temperature of the exhaust gas to be lower than 100° C. in all of the flow paths of the exhaust gas analyzing apparatus 5. In order to obtain the effect of the present invention, it is sufficient that the temperature of at least a part of the exhaust gas is temperature-regulated to be lower than 100° C. and higher than a boiling point which is determined from the pressure of the pressure-reduced exhaust gas.

Although the CO.CO2 analyzer 51 is used as a moisture concentration meter in the previous described embodiment, those using the other measurement principles or even not measuring carbon monoxide and carbon dioxide may be used as the moisture concentration meter. As the analyzer, it is sufficient to analyze the components of the exhaust gas and the measurement target and the measurement principle are not limited to those of the previous described embodiment.

Although the temperature setting part 82 of the previous described embodiment is adapted to change the set temperature depending on an operation input by a user, the set temperature may be automatically changed.

Figure 4:
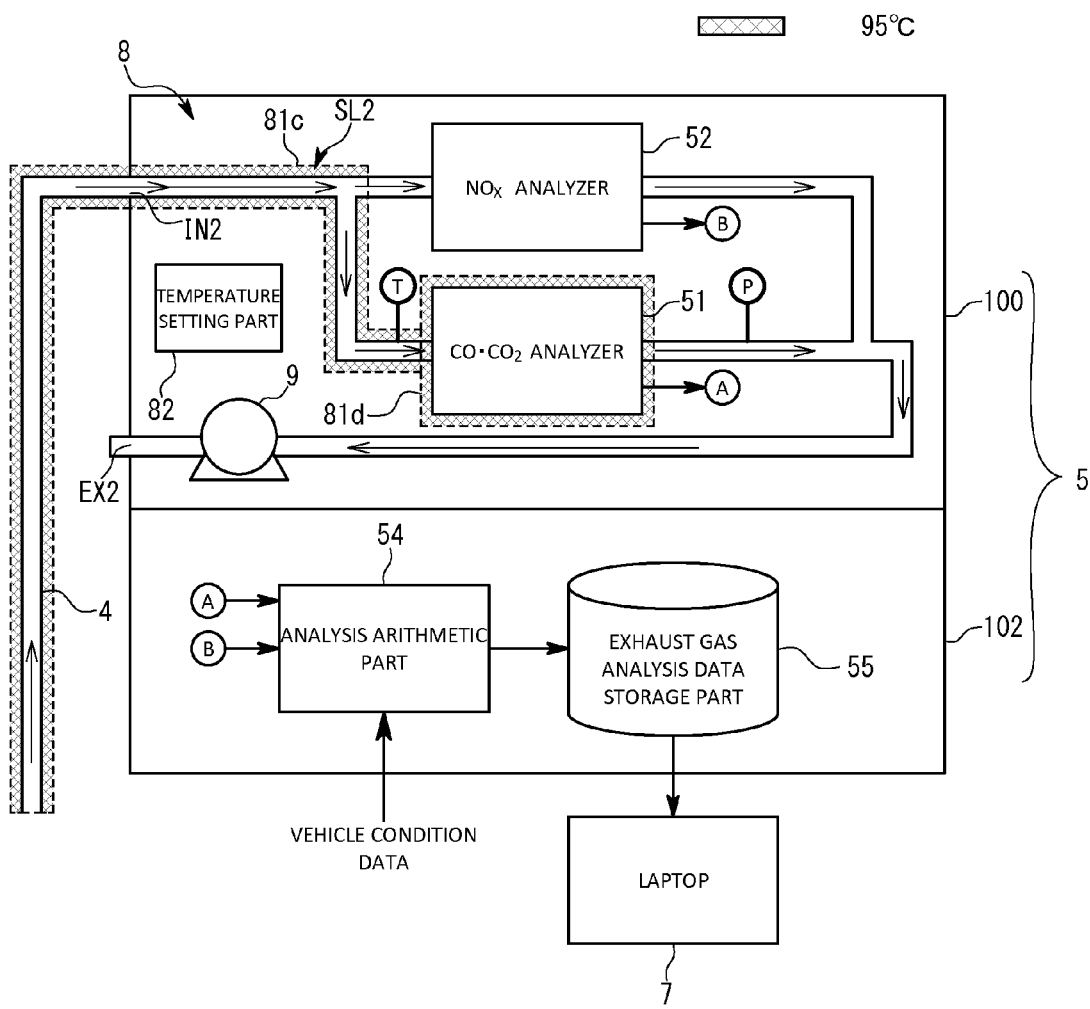
FIG. 4 is a schematic diagram showing details of an exhaust gas analyzing apparatus according to further another embodiment of the present invention.

For example, in the previous described embodiment as shown in FIG. 4, it may be configured that, a thermometer T and a pressure gauge P are further provided in the vicinity of the CO.CO2 analyzer 51, and the temperature setting part 82 is adapted to change the set temperature to be set to the heating wire heater 81 during the exhaust gas analysis, depending on the temperature and pressure measured by thermometer T and the pressure gauge P, respectively. With this configuration, since the boiling point of the current water is known from the pressure measured by the pressure gauge P, not only the lowest temperature required for preventing the condensation of the moisture from occurring is known but also it becomes possible to appropriately control whether the temperature regulation should be strengthened or weakened in comparison with the current temperature.

For example, the temperature setting part 82 may be configured to change the set temperature depending on the atmospheric pressure. With this configuration, when the exhaust gas is analyzed in a high pressure area where the moisture is hard to be evaporated, it is possible to reliably prevent the bad influence on the analysis due to the condensation of the moisture by regulating the set temperature to be high. On the other hand, when the exhaust gas is analyzed in a low pressure area such as a high land where the moisture is easy to be evaporated, it is possible to further reduce the power consumption in the temperature regulation mechanism 8 while preventing the condensation by regulating the set temperature to be low.

In the case where a large amount of moisture is contained in the exhaust gas, the condensation becomes easy to occur. In consideration of this point, in order to be able to prevent the condensation and finely control the reduction of the power consumption, it is sufficient that the temperature setting part 82 is configured to change the set temperature in accordance with a type of the internal combustion engine 1 of the vehicle VH. For example, since a large amount of moisture is contained in the exhaust gas of a diesel engine compared to a gasoline engine, it is sufficient that the temperature setting part 82 is configured to set the first temperature in the case of analyzing the exhaust gas of a diesel engine to be higher than the first temperature to be used for a gasoline engine.

In addition, even in the case where the moisture contained in the exhaust gas is temporarily increases due to some abnormality of the engine, in order to be able to quickly eliminate the influence of the moisture from the exhaust gas analyzing apparatus 5 and resume the analysis in a short time, it is sufficient to be configured that the set temperature can be changed in accordance with an indication value of the moisture concentration meter. For example, in the case where an indication value in the moisture concentration meter becomes higher than a threshold, it is sufficient that the set temperature is raised to be high to thereby allow the moisture to be easily evaporated.

Figure 5:
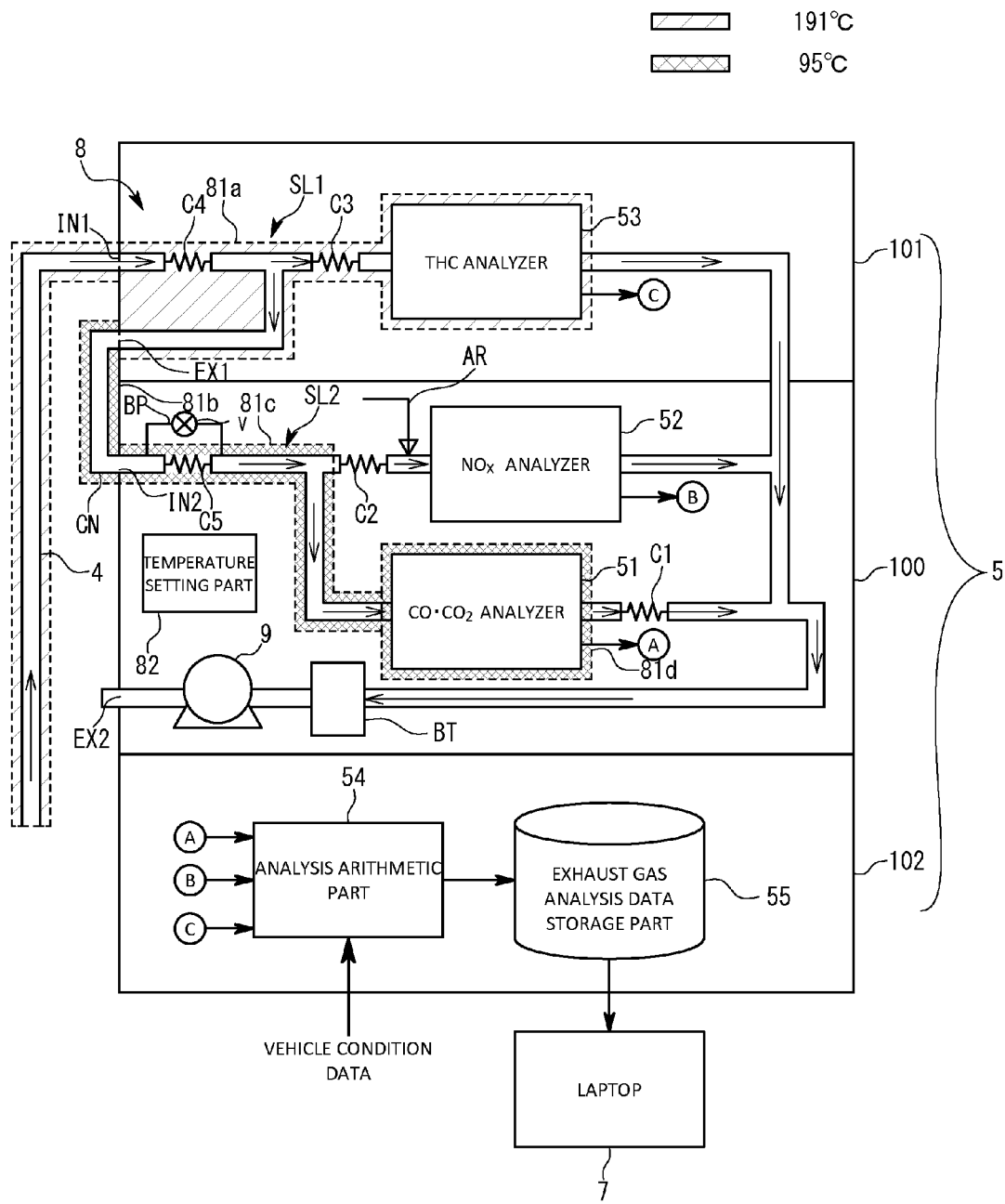
FIG. 5 is a schematic diagram showing details of an exhaust gas analyzing apparatus according to other embodiment of the present invention.

FIG. 5 shows the fourth embodiment of the present invention. Note that members or parts corresponding to those of the previous described embodiments are denoted by the same reference numerals. In this embodiment, for the purposes of regulation of a flow rate of exhaust gas flowing into each equipment, reduction of influences on the measurements due to fluctuation and pulsation of the pressure and improvement of the measurement accuracy by varying the pressure of the exhaust gas in each of the analyzers, there is provided a capillary in each of the flow paths.

More specifically, a first capillary C1 is provided in an outlet side flow path of the CO.CO2 analyzer 51, a second capillary C2 is provided in an inlet side flow path of the NOX analyzer 52, a third capillary C3 is provided in an inlet side flow path of the THC analyzer 53, a fourth capillary C4 is provided in the vicinity of the exhaust gas introduction terminal IN1 of the extension analysis unit 101, and a fifth capillary C5 is provided in the vicinity of the exhaust gas introduction terminal IN2 of the main body 100.

Regarding the pressure reducing actions of the pressure reduction source 9 which is a suction pump provided in the downstream side of the analyzers 51 to 53, by providing the first capillary C1 in the outlet side flow path of the CO.CO2 analyzer 51, and providing the second and third capillaries C2 and C3 respectively in the inlet side flow paths of the NOX analyzer 52 and the THC analyzer 53, the pressure reducing actions for the NOX analyzer 52 and the THC analyzer 53 are intended to be exhibited more significantly than that for the CO.CO2 analyzer 51. For this reason, whereas the internal pressure of the CO.CO2 analyzer 51 is in a degree of −20 kPa with respect to the atmospheric pressure, the internal pressures of the NOX analyzer 52 and the THC analyzer 53 are to be kept −40 kPa with respect to the atmospheric pressure. That is, since the analytical precision becomes higher as the pressures of the NOX analyzer 52 and the THC analyzer 53 are lower, the analytical precision can be improved by this configuration. Further, since the CO.CO2 analyzer 51 which is hard to be influenced by the pressure has a larger internal volume compared to those of the other analyzers 52 and 53, the capacity of the pressure reduction source 9 need not be increased by avoiding the pressure from lowering to be too small. Thus, by reduction in size and labor-saving, it becomes easy to configure as the vehicle mounted type exhaust gas analyzing apparatus 5 with sufficient analytical precision.

In order to reduce the influence of the pressure fluctuation from the outside in the case where the fourth and fifth capillaries C4 and C5 are connected to the hot hose 4, the fourth and fifth capillaries C4 and C5 are provided in order to keep the internal pressure of the exhaust gas analyzing apparatus 5 to be low. Note that, as shown in FIG. 5, in the case where the extension analysis unit 101 is attached but the hot hose 4 is not attached to the main body 100, an opening/closing valve V provided on a bypass BP bypassing the fifth capillary C5 is opened to thereby avoid the fifth capillary C5 from operating. Note that, as the previous described embodiments shown in FIGS. 3 and 4, in the case where the hot hose 4 is directly attached to the main body 100, the opening/closing valve V is closed to thereby allow the fifth capillary C5 to be operable.

Further, an air injecting mechanism AR is provided in a subsequent stage of the second capillary C2 in the inlet side flow path of the NOX analyzer 52 to thereby dilute the exhaust gas flowing into the NOX analyzer 52 and prevent the condensation of moisture.

Further, a buffer tank BT is provided in front of the pressure reduction source 9 to thereby less affect the respective analyzers by the pulsation generated by the pressure reduction source 9.

With the configuration as shown in FIG. 5, even a single pressure reduction source 9 having a not so large capacity can separately keep the pressures suitable for the measurements in the respective analyzers using a plurality of kinds of the measurement principles, and thus the vehicle mounted type exhaust gas analyzing apparatus 5 can be made more preferable.

In addition, various modifications and combinations of the embodiments can be made without departing from the spirit of the present invention.

REFERENCE SIGNS LIST

200 . . . Exhaust gas analyzing system
100 . . . Exhaust gas analyzing apparatus main body
101 . . . Extension analysis unit
102 . . . Arithmetic storage unit
1 . . . Internal combustion engine
2 . . . Exhaust pipe
3 . . . Exhaust gas sampling mechanism
4 . . . Hot hose
5 . . . Exhaust gas analyzing apparatus
51 . . . CO.CO2 analyzer (moisture concentration meter)
52 . . . NOX analyzer
53 . . . THC analyzer
54 . . . Analysis arithmetic part
55 . . . Exhaust gas analysis data storage part
6 . . . Power switching device
7 . . . Laptop
8 . . . Temperature-regulating mechanism
81 . . . Heating wire heater
82 . . . Temperature setting part
SL1 . . . First sampling line
SL2 . . . Second sampling line
CN . . . Connection pipe

What is claimed is:

1. An exhaust gas analyzing apparatus of a vehicle mounted type equipped with one or multiple analyzers that are configured to analyze components contained in exhaust gas, comprising:
an exhaust gas introduction terminal that is connected to a hot hose;
a sampling line that is an exhaust gas flow path extending from the exhaust gas introduction terminal that is configured to introduce the exhaust gas from the outside to the one or multiples analyzers;
a single pressure reduction source that is arranged downstream of the one or multiple analyzers and that is configured to reduce a pressure in the sampling line to a predetermined pressure;
a pressure sensor that is arranged between the one or multiple analyzers and pressure reduction source; and
a temperature-regulating mechanism that is configured to regulate a temperature of the exhaust gas flowing in the sampling line to be at least a first temperature during normal analysis of the exhaust gas, and regulate the temperature of the exhaust gas to be at least a second temperature greater than the first temperature during cold start operation of the vehicle prior to the normal analysis of the exhaust gas,
wherein the first temperature is set to be a temperature equal to or greater than an evaporation temperature of moisture at a reduced predetermined pressure and lower than an evaporation temperature of moisture at one atmospheric pressure.

2. The exhaust gas analyzing apparatus according to claim 1, wherein the temperature-regulating mechanism is equipped with a heating wire heater that is configured to regulate a temperature of the sampling line and a temperature setting part that is configured to set a set temperature which is a target value to be set to the heating wire heater, and wherein
the temperature setting part is configured to change the set temperature in accordance with an atmospheric pressure.

3. The exhaust gas analyzing apparatus according to claim 2, wherein the temperature setting part is configured to change the set temperature in accordance with a type of an internal combustion engine of the vehicle.

4. The exhaust gas analyzing apparatus according to claim 2, wherein the one or multiple analyzers are adapted to analyze a concentration of moisture contained in the exhaust gas, and wherein
the temperature setting part is configured to change the set temperature in accordance with an indication value of the one or multiple analyzers.

5. The exhaust gas analyzing apparatus according to claim 1, wherein the temperature-regulating mechanism is configured to change the temperature based on a pressure value that is measured by the pressure sensor.

6. The exhaust gas analyzing apparatus according to claim 1 further comprising:
one or multiple capillaries provided in an inlet side flow path or an outlet side flow path of the one or multiple analyzers.

7. The exhaust gas analyzing apparatus according to claim 6, wherein,
the multiple analyzers include:
a CO CO2 analyzer that is adapted to analyze a concentration of CO or CO2 contained in the exhaust gas; and
a NOx analyzer that is adapted to analyze a concentration of NOx contained in the exhaust gas; and
the multiple capillaries include:
a first capillary that is provided between an outlet side of the CO CO2 analyzer and the reduction source; and
a second capillary that is provided in an inlet side of the NOx analyzer.

8. The exhaust gas analyzing apparatus according to claim 7, wherein,
the multiple analyzers further include:
a THC analyzer that is adapted to analyzer a concentration of THC contained in the exhaust gas; and
the multiple capillaries further include:
a third capillary that is provided in an inlet side of the THC analyzer.

9. The exhaust gas analyzing apparatus according to claim 8, wherein,
the multiple capillaries further include:
a fourth capillary that is provided between the exhaust gas introduction terminal and the THC analyzer.

10. The exhaust gas analyzing apparatus according to claim 7, wherein,
the multiple capillaries further include:
a fifth capillary that is provided between the exhaust gas introduction terminal and the CO CO2 analyzer or the NOx analyzer.

11. An exhaust gas analyzing method using an exhaust gas analyzing apparatus of a vehicle mounted type equipped with one or multiple analyzers that are configured to analyze components contained in exhaust gas, wherein the exhaust gas analyzing apparatus includes an exhaust gas introduction terminal that is connected to a hot hose, a sampling line that is an exhaust gas flow path extending from the exhaust gas introduction terminal and that is configured to introduce the exhaust gas from the outside to the one or multiple analyzers, a single pressure reduction source that is arranged downstream of the one or multiple analyzers and that is configured to reduce a pressure in the sampling line to a predetermined pressure, a pressures sensor that is arranged between the one or multiple analyzers and pressure reduction source, and a temperature-regulating mechanism, the method comprising:

regulating via the temperature-regulating mechanism a temperature of the exhaust gas flowing in the sampling line to be at least a first temperature, equal to or greater than an evaporation temperature of moisture at a reduced predetermined pressure and lower than an evaporation temperature of moisture at one atmospheric pressure, during normal analysis of the exhaust gas, and regulating via the temperature-regulating mechanism the temperature of the exhaust gas flowing in the sampling line to be at least a second temperature greater than the first temperature during cold start operation of a vehicle prior to the normal analysis of the exhaust gas.

* * * * *